(12) United States Patent
Mimura et al.

(10) Patent No.: US 9,879,037 B2
(45) Date of Patent: Jan. 30, 2018

(54) FLUORINE-CONTAINING PHOSPHATE ESTER-AMIDE, AND FLAME RETARDANT RESIN, FLAME RETARDANT LIQUID AND FLAME RETARDANT SOLVENT FOR ORGANIC SYNTHESIS CONTAINING SAME

(71) Applicant: TOSOH F-TECH, INC., Shunan-shi (JP)

(72) Inventors: Hideyuki Mimura, Shunan (JP); Hiroaki Fujita, Shunan (JP); Hisao Eguchi, Shunan (JP)

(73) Assignee: TOSOH F-TECH, INC., Shunan-shi (JP)

( * ) Notice: Subject to any disclaimer, the term of this patent is extended or adjusted under 35 U.S.C. 154(b) by 181 days.

(21) Appl. No.: 14/385,862

(22) PCT Filed: Mar. 22, 2013

(86) PCT No.: PCT/JP2013/001951
§ 371 (c)(1),
(2) Date: Sep. 17, 2014

(87) PCT Pub. No.: WO2013/145669
PCT Pub. Date: Oct. 3, 2013

(65) Prior Publication Data
US 2015/0053901 A1      Feb. 26, 2015

(30) Foreign Application Priority Data

Mar. 30, 2012  (JP) .................. 2012-078732
Dec. 3, 2012   (JP) .................. 2012-264153

(51) Int. Cl.
| | |
|---|---|
| *C07F 9/59* | (2006.01) |
| *H01M 10/42* | (2006.01) |
| *H01M 10/0567* | (2010.01) |
| *C08J 9/00* | (2006.01) |
| *C09K 21/12* | (2006.01) |
| *C07F 9/24* | (2006.01) |
| *H01M 10/0525* | (2010.01) |
| *C08G 18/24* | (2006.01) |
| *C08G 18/32* | (2006.01) |
| *C08G 18/72* | (2006.01) |

(52) U.S. Cl.
CPC .............. *C07F 9/59* (2013.01); *C07F 9/2408* (2013.01); *C07F 9/2454* (2013.01); *C07F 9/2458* (2013.01); *C07F 9/591* (2013.01); *C08G 18/24* (2013.01); *C08G 18/32* (2013.01); *C08G 18/72* (2013.01); *C08J 9/0038* (2013.01); *C09K 21/12* (2013.01); *H01M 10/0525* (2013.01); *H01M 10/0567* (2013.01); *H01M 10/4235* (2013.01); *C08J 2375/04* (2013.01)

(58) Field of Classification Search
CPC ........ C07F 9/59; C07F 9/2454; C07F 9/2458; C07F 9/2408; C07F 9/591; H01M 10/0567; H01M 10/4235; H01M 10/0525; C08G 18/72; C08G 18/32; C08G 18/24; C08J 9/0038; C08J 2375/04; C09K 21/12; Y02E 60/122

See application file for complete search history.

(56) References Cited

FOREIGN PATENT DOCUMENTS

| | | | |
|---|---|---|---|
| JP | 54-019919 | A | 2/1979 |
| JP | 57-207642 | A | 12/1982 |
| JP | 05-222070 | A | 8/1993 |
| JP | 08-088023 | A | 4/1996 |
| JP | 11-181428 | A | 7/1999 |
| JP | 2001-139823 | A | 5/2001 |
| JP | 2001139823 | A * | 5/2001 |

(Continued)

OTHER PUBLICATIONS

English Translation of JP 2011141974.*
English Translation of JP 2001-139823.*
International Search Report dated May 14, 2013 in PCT/JP2013/001951 filed Mar. 22, 2013.

(Continued)

*Primary Examiner* — Peter F Godenschwager
*Assistant Examiner* — Andrew J. Oyer
(74) *Attorney, Agent, or Firm* — Oblon, McClelland, Maier & Neustadt, L.L.P.

(57) ABSTRACT

[Problem] To provide a fluorine-containing phosphate ester-amide which has high flame retardancy such as exhibiting flame retardant effects at a small quantity of addition, and sufficient hydrolysis resistance.
[Solution] A fluorine-containing phosphate ester-amide represented by general formula (1). (In the formula, R1 and R2 are the same or different and represent a branched or linear alkyl group having 1 to 20 carbon atoms in which at least one carbon bonded to a nitrogen atom is a secondary or tertiary carbon, wherein R1 and R2 may have a substituent group selected from the group consisting of an alkoxy group, a hydroxy group, an amino group, a methyl amino group, an ethyl amino group, a dimethyl amino group, diethyl amino group and a fluorine atom. In addition, R1 and R2 may be bonded together to form a five- to eight-membered cyclic structure. X and Y are the same or different and represent a hydrogen atom or a fluorine atom, and n and m represent an integer of 1 to 6.)

$$X {\left(\begin{array}{c}F\\|\\|\\F\end{array}\begin{array}{c}H\\|\\|\\H\end{array}\right)}_{n} O - \underset{\underset{R^1 \diagup N \diagdown R^2}{|}}{\overset{\overset{O}{\|}}{P}} - O {\left(\begin{array}{c}H\\|\\|\\H\end{array}\begin{array}{c}F\\|\\|\\F\end{array}\right)}_{m} Y \qquad (1)$$

12 Claims, No Drawings

(56) References Cited

FOREIGN PATENT DOCUMENTS

| JP | 2001-192746 A | 7/2001 |
| JP | 2002-203597 A | 7/2002 |
| JP | 2008-519146 A | 6/2008 |
| JP | 2009-102576 A | 5/2009 |
| JP | 2011-141974 A | 7/2011 |
| JP | 2011141974 A * | 7/2011 |
| WO | 01/04204 A1 | 1/2001 |
| WO | 2006/052606 A2 | 5/2006 |

OTHER PUBLICATIONS

Christopher M. Timperley, et al., "Fluorinated phosphorus compounds Part 7. The reactions of bis(fluoroalkyl) phosphorochloridates with nitrogen nucleophiles" Journal of Fluorine Chemistry, vol. 113, No. 1, 2002, pp. 111-122.

Christopher M. Timperley, et al., "Fluorinated phosphorus compounds Part 1. The synthesis and reactions of some fluoroalkyl phosphoryl compounds" Journal of Fluorine Chemistry, vol. 104, No. 2, 2000, pp. 215-223.

International Preliminary Report on Patentability and Written Opinion dated Oct. 9, 2014 in PCT/JP2013/001951.

* cited by examiner

FLUORINE-CONTAINING PHOSPHATE ESTER-AMIDE, AND FLAME RETARDANT RESIN, FLAME RETARDANT LIQUID AND FLAME RETARDANT SOLVENT FOR ORGANIC SYNTHESIS CONTAINING SAME

TECHNICAL FIELD

The present invention relates to fluorine-containing phosphate ester-amides. More particularly, the present invention relates to a fluorine-containing phosphate ester-amide having high hydrolysis resistance and useful in applications such as flame retardants for resins, flame retardants for flammable liquids, flame retardant solvents for organic synthesis, flame retardant solvents for secondary battery electrolytes, flame retardant hydraulic fluids, flame retardant lubricants, flame retardant extractants, and flame retardant cleaning agents. The present invention also relates to a flame retardant resin, a flame retardant liquid, and a flame retardant solvent for organic synthesis, each of which contains the fluorine-containing phosphate ester-amide.

BACKGROUND ART

Phosphate esters and other phosphate esters such as phosphate ester-amides have excellent flame retardancy and self-extinguishing properties resulting from phosphorus atoms and are therefore widely used as flame retardants for various resins (for example, Patent Literatures 1 to 3).

As the flame retardant applications diversify, the phosphate esters are required to have higher performance. More specifically, in order to reduce influences on the physical properties and functions of substances to which the phosphate esters are added, the phosphate esters are required to exhibit their flame retardant effect with a smaller amount of addition and to have chemical and thermal stability so that the phosphate esters are less likely to degenerate even in high-temperature conditions.

One particular problem of the phosphate esters is that they easily undergo hydrolysis because of their chemical stability. When phosphate esters undergo hydrolysis, problems occur in that flame retardancy deteriorates or disappears and that acidity derived from phosphoric acid may exert an influence on the performance and durability of substances to which the phosphate esters are added. To address these problems, phosphate esters with various structures have been proposed (for example, Patent Literatures 4 and 5) to improve hydrolysis resistance. However, the task of improving flame retardancy so that the flame retardant effect is achieved with a small amount of addition still remains.

Among the phosphate esters, relatively low-molecular weight compounds that are in liquid form at room temperature are used not only as flame retardants for resins but also for various applications such as a flame retardant for an electrolyte for a lithium ion secondary battery (Patent Literature 6), a hydraulic fluid (Patent Literature 7), an extractant (Patent Literature 8), and a solvent for organic synthesis (Patent Literature 9). Trimethyl phosphate, tributyl phosphate, etc. are used as the above phosphate esters. However, their resistance to hydrolysis is insufficient, and they are flammable materials with flash points, so that their flame retardant effect is insufficient.

Phosphate esters having fluorine atoms in their ester side chains are known to have high flame retardancy due to the synergistic effect of the phosphorus and fluorine atoms and to exhibit the flame retardant effect even with a smaller amount of addition (Non-Patent Literature 1). The fluorine-containing phosphate esters also have a feature in that resistance to oxidation is high and are therefore contemplated to be used mainly as flame retardants for an electrolyte for a lithium ion secondary battery that is required to have particularly high safety and oxidation resistance (Non-Patent Literature 1, Patent Literature 10).

However, the hydrolysis resistance of the fluorine-containing phosphate esters is rather low because of the influence of the electron-withdrawing fluorine atoms. In addition, since a phosphate diester, which is a hydrolysis product, exhibits strong acidity (Non-Patent Literature 2), hydrolysis is likely to be accelerated with the phosphate diester acting as a catalyst. Therefore, the fluorine-containing phosphate esters have a problem with duration of flame retardancy when used as flame retardants for resins and also have a problem in that use conditions are limited when they are used as extractants or solvents for organic synthesis. Also in the secondary battery electrolyte application, the influence of moisture introduced from various components is not negligible, and the generation of a phosphate diester by hydrolysis causes an adverse effect on battery performance.

Among the fluorine-containing phosphate esters, fluorine-containing phosphate ester-amides having a P—N bond in their molecule are known (Non-Patent Literature 3, Patent Literature 11). With such a fluorine-containing phosphate ester-amide, an amine is generated when the P—N bond is broken by hydrolysis, and therefore the phosphate diester is neutralized. Therefore, the influence of the above-described acid catalytic action is reduced, and it is expected that the fluorine-containing phosphate ester-amide has improved hydrolysis resistance. Unsubstituted alkyl groups and linear alkyl groups have been reported as substituents for the amide moiety of the fluorine-containing phosphate ester-amide.

Perfluoroalkyl compounds such as perfluorohexane, perfluoroalkyl ethers, and perfluoroalkyl amines are known as compounds that have no flash point and are substantially not degraded by hydrolysis. These compounds are used mainly as dewatering agents for an industrial parts washing process on the basis of low latent heat of vaporization of these compounds. However, since the compatibility of these perfluoroalkyl compounds with various organic compounds is not sufficient, it is difficult to use the perfluoroalkyl compounds in a wide range of applications such as flame retardants for resins, solvents for organic synthesis, flame retardants for an electrolyte for a secondary battery, and extractants.

CITATION LIST

Patent Literature

Patent Literature 1: JPS54-19919
Patent Literature 2: JPH11-181428
Patent Literature 3: JP2001-139823
Patent Literature 4: JPS57-207642
Patent Literature 5: WO01/4204
Patent Literature 6: JP2002-203597
Patent Literature 7: JP2008-519146
Patent Literature 8: JP2001-192746
Patent Literature 9: JP2009-102576
Patent Literature 10: JPH8-88023
Patent Literature 11: JP2011-141974

Non-Patent Literature

Non-Patent Literature 1: J. Electrochemical Society, 150, A161-169 (2003)
Non-Patent Literature 2: Seriya Khimicheskaya, 1491-1497 (1982)
Non-Patent Literature 3: J. Fluorine Chemistry, 113, 111-122 (2002)

SUMMARY OF INVENTION

Technical Problem

As described above, phosphate esters have the problem of improvement of flame retardancy and the problem of hydrolysis resistance, and fluorine-containing phosphate ester-amides have the possibility of solving these problems. However, the present inventors have examined the hydrolysis resistance of the fluorine-containing phosphate ester-amides shown in the prior art documents and found that the hydrolysis resistance is still insufficient.

The present invention has been made in view of the above problems. Accordingly, it is an object thereof to provide a fluorine-containing phosphate ester-amide having high flame retardancy, i.e., for example, exhibiting its flame retardant effect even with a small amount of addition, and also having sufficient hydrolysis resistance.

Solution to Problem

The present inventors have conducted extensive studies in order to solve the above problems and found that a fluorine-containing phosphate ester-amide having a specific structure exhibits its flame retardant effect even with a small amount of addition and also has much superior hydrolysis resistance. Thus, the present invention has been completed. Accordingly, the present invention relates to the following aspects.

1. A fluorine-containing phosphate ester-amide represented by the following general formula (1)

[Chemical formula 1]

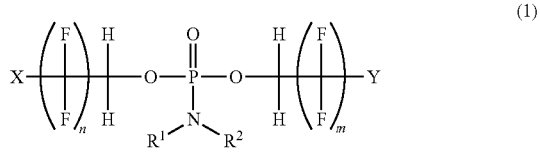

(1)

(wherein, in the general formula (1), $R^1$ and $R^2$ are the same or different and each represent a branched or linear alkyl group having 1 to 20 carbon atoms; in at least one of $R^1$ and $R^2$, a carbon atom bonded to a nitrogen atom is a secondary carbon or a tertiary carbon; $R^1$ and $R^2$ may have a substituent selected from the group consisting of an alkoxy group, a hydroxy group, an amino group, a methyl amino group, an ethyl amino group, a dimethyl amino group, a diethyl amino group, and a fluorine atom; $R^1$ and $R^2$ may be bonded together to form a five- to eight-membered cyclic structure; X and Y are the same or different and each represent a hydrogen atom or a fluorine atom; and n and m each represent an integer of 1 to 6).

2. The fluorine-containing phosphate ester-amide according to 1, wherein the fluorine-containing phosphate ester-amide is represented by the following general formula (2)

[Chemical formula 2]

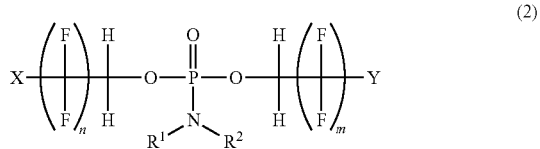

(2)

(wherein, in the general formula (2), $R^1$ and $R^2$ are the same or different and each represent a branched alkyl group having 3 to 20 carbon atoms; in each of $R^1$ and $R^2$, a carbon atom bonded to a nitrogen atom is a secondary carbon or a tertiary carbon; $R^1$ and $R^2$ may have a substituent selected from the group consisting of an alkoxy group, a hydroxy group, an amino group, a methyl amino group, an ethyl amino group, a dimethyl amino group, a diethyl amino group, and a fluorine atom; $R^1$ and $R^2$ may be bonded together to form a five- to eight-membered cyclic structure; X and Y are the same or different and each represent a hydrogen atom or a fluorine atom; and n and m each represent an integer of 1 to 6).

3. A flame retardant resin containing the fluorine-containing phosphate ester-amide represented by the general formula (1) and/or the fluorine-containing phosphate ester-amide represented by the general formula (2).

4. A flame retardant liquid containing a fluorine-containing phosphate ester-amide represented by the general formula (1) and/or the fluorine-containing phosphate ester-amide represented by the general formula (2).

5. A flame retardant solvent for organic synthesis, consisting of the fluorine-containing phosphate ester-amide represented by the general formula (1) and/or the fluorine-containing phosphate ester-amide represented by the general formula (2) or the flame retardant liquid according to 4.

Advantageous Effects of Invention

The present invention provides a fluorine-containing phosphate ester-amide having superior flame retardancy, i.e., for example, exhibiting its flame retardant effect even with a small amount of addition, and also having much superior hydrolysis resistance. A resin capable of maintaining a flame retardant effect for a long time can be obtained by adding a small amount of the fluorine-containing phosphate ester-amide to the resin. The fluorine-containing phosphate ester-amide provided by the present invention and having a specific structure has superior flame retardancy and superior hydrolysis resistance and also has the following and other features. The fluorine-containing phosphate ester-amide is in a liquid state over a wide temperature range, has a relatively high dielectric constant, and has high compatibility with organic compounds. Therefore, a flame retardant liquid composed only of the fluorine-containing phosphate ester-amide or containing a flammable liquid and the fluorine-containing phosphate ester-amide added thereto is provided and can be used for various applications such as flame retardant solvents for organic synthesis and flame retardant electrolytes for secondary batteries.

DESCRIPTION OF EMBODIMENTS

The fluorine-containing phosphate ester-amide of the present invention is represented by the above general formula (1). Specifically, the fluorine-containing phosphate ester-amide is characterized by having at least one branched alkyl group that has a secondary or tertiary carbon bonded to the nitrogen atom in the amide moiety. It is expected that fluorine-containing phosphate esters do not originally have sufficient resistance to hydrolysis because of the influence of the electron-withdrawing properties of fluorine atoms. However, the fluorine-containing phosphate ester-amide of the present invention having a branched structure in the amide moiety has significantly improved resistance to hydrolysis. The reason for the surprisingly significant effect is not clear but may be due to the synergistic effect of the electronic and steric effects resulting from the above structure.

Examples of $R^1$ and $R^2$ in the general formula (1) may include a methyl group, an ethyl group, a n-propyl group, an isopropyl group, a n-butyl group, an isobutyl group, a sec-butyl group, a t-butyl group, a n-amyl group, a t-amyl group, a n-hexyl group, a cyclohexyl group, a n-octyl group, a cyclooctyl group, a 2-ethylhexyl group, a n-decyl group, a n-dodecyl group, a n-tetradecyl group, a n-hexadecyl group, a n-octadecyl group, a n-eicosyl group, a 2-methoxyethyl group, a 2-ethoxyethyl group, a 2-hydroxyethyl group, a 2-aminoethyl group, a 2-(methylamino)ethyl group, a 2-(dimethylamino)ethyl group, a 2-(ethylamino)ethyl group, a 2-(diethylamino)ethyl group, a 2,2,2-trifluoroethyl group, a 2-methoxy-1-methylethyl group, a 2-ethoxy-1-methylethyl group, a 2-hydroxy-1-methylethyl group, a 2-amino-1-methylethyl group, a 2-(methylamino)-1-methylethyl group, a 2-(dimethylamino)-1-methylethyl group, a 2-(ethylamino)-1-methylethyl group, a 2-(diethylamino)-1-methylethyl group, a 2-methoxy-1,1-dimethylethyl group, a 2-ethoxy-1,1-dimethylethyl group, a 2-hydroxy-1,1-dimethylethyl group, a 2-amino-1,1-dimethylethyl group, a 2-(methylamino)-1,1-dimethylethyl group, a 2-(dimethylamino)-1,1-dimethylethyl group, a 2-(ethylamino)-1,1-dimethylethyl group, and a 2-(diethylamino)-1,1-dimethylethyl group.

In the general formula (1), X and Y are the same or different and each represent a hydrogen atom or a fluorine atom, and n and m each represent an integer of 1 to 6. Examples of the fluorine-containing phosphate ester-amide represented by the general formula (1) may include phosphoric acid bis(2,2,2-trifluoroethyl) N-isopropylmethylamide, phosphoric acid bis(2,2,2-trifluoroethyl) N-isopropylethylamide, phosphoric acid bis(2,2,2-trifluoroethyl) N-isopropyl-n-propylamide, phosphoric acid bis(2,2,2-trifluoroethyl) diisopropylamide, phosphoric acid bis(2,2,2-trifluoroethyl) N-isopropyl-n-butylamide, phosphoric acid bis(2,2,2-trifluoroethyl) N-isopropyl-n-amylamide, phosphoric acid bis(2,2,2-trifluoroethyl) N-isopropyl-n-hexylamide, phosphoric acid bis(2,2,2-trifluoroethyl) N-isopropylcyclohexylamide, phosphoric acid bis(2,2,2-trifluoroethyl) N-isopropyl-n-octylamide, phosphoric acid bis(2,2,2-trifluoroethyl) N-isopropylcyclooctylamide, phosphoric acid bis(2,2,2-trifluoroethyl) N-isopropyl-n-decylamide, phosphoric acid bis(2,2,2-trifluoroethyl) N-isopropyl-n-dodecylamide, phosphoric acid bis(2,2,2-trifluoroethyl) N-isopropyl-n-tetradecylamide, phosphoric acid bis(2,2,2-trifluoroethyl) N-isopropyl-n-hexadecylamide, phosphoric acid bis(2,2,2-trifluoroethyl) N-isopropyl-n-octadecylamide, phosphoric acid bis(2,2,2-trifluoroethyl) N-isopropyl-n-eicosylamide, phosphoric acid bis(2,2,2-trifluoroethyl) N-isopropyl-2-methoxyethylamide, phosphoric acid bis(2,2,2-trifluoroethyl) N-isopropyl-2-ethoxyethylamide, phosphoric acid bis(2,2,2-trifluoroethyl) N-isopropyl-2-hydroxyethylamide, phosphoric acid bis(2,2,2-trifluoroethyl) N-isopropyl-2-aminoethylamide, phosphoric acid bis(2,2,2-trifluoroethyl) N-isopropyl-2-(methylamino)ethylamide, phosphoric acid bis(2,2,2-trifluoroethyl) N-isopropyl-2-(dimethylamino)ethylamide, phosphoric acid bis(2,2,2-trifluoroethyl) N-isopropyl-2-(ethylamino)ethylamide, phosphoric acid bis(2,2,2-trifluoroethyl) N-isopropyl-2-(diethylamino)ethylamide, phosphoric acid bis(2,2,2-trifluoroethyl) N-isopropyl-2,2,2-trifluoroethylamide, phosphoric acid bis(2,2,2-trifluoroethyl) N-(2-methoxy-1-methylethyl)methylamide, phosphoric acid bis(2,2,2-trifluoroethyl) N-(2-methoxy-1-methylethyl)isopropylamide, phosphoric acid bis(2,2,2-trifluoroethyl) N-(2-hydroxy-1-methylethyl)methylamide, phosphoric acid bis(2,2,2-trifluoroethyl) N-(2-hydroxy-1-methylethyl)isopropylamide, phosphoric acid bis(2,2,2-trifluoroethyl) N-(2-amino-1-methylethyl)methylamide, phosphoric acid bis(2,2,2-trifluoroethyl) N-(2-amino-1-methylethyl)isopropylamide, phosphoric acid bis(2,2,2-trifluoroethyl) N-[2-(methylamino)-1-methylethyl]methylamide, phosphoric acid bis(2,2,2-trifluoroethyl) N-[2-(methylamino)-1-methylethyl]isopropylamide, phosphoric acid bis(2,2,2-trifluoroethyl) N-[2-(dimethylamino)-1-methylethyl]methylamide, phosphoric acid bis(2,2,2-trifluoroethyl) N-[2-(dimethylamino)-1-methylethyl]isopropylamide, phosphoric acid bis(2,2,2-trifluoroethyl) N-sec-butylmethylamide, phosphoric acid bis(2,2,2-trifluoroethyl) N-sec-butylethylamide, phosphoric acid bis(2,2,2-trifluoroethyl) N-sec-butyl-n-propylamide, phosphoric acid bis(2,2,2-trifluoroethyl) N-sec-butylisopropylamide, phosphoric acid bis(2,2,2-trifluoroethyl) N-sec-butyl-n-butylamide, phosphoric acid bis(2,2,2-trifluoroethyl) di-sec-butylamide, phosphoric acid bis(2,2,2-trifluoroethyl) N-sec-butyl-t-butylamide, phosphoric acid bis(2,2,2-trifluoroethyl) N-t-butylmethylamide, phosphoric acid bis(2,2,2-trifluoroethyl) N-t-butylethylamide, phosphoric acid bis(2,2,2-trifluoroethyl) N-t-butyl-n-propylamide, phosphoric acid bis(2,2,2-trifluoroethyl) N-t-butylisopropylamide, phosphoric acid bis(2,2,2-trifluoroethyl) N-t-butyl-n-butylamide, phosphoric acid bis(2,2,2-trifluoroethyl) di-t-butylamide, phosphoric acid bis(2,2,2-trifluoroethyl) N-t-amylmethylamide, phosphoric acid bis(2,2,2-trifluoroethyl) N-t-amylisopropylamide, phosphoric acid bis(2,2-difluoroethyl) N-isopropylmethylamide, phosphoric acid bis(2,2-difluoroethyl) diisopropylamide, phosphoric acid bis(2,2,3,3-tetrafluoropropyl) N-isopropylmethylamide, phosphoric acid bis(2,2,3,3-tetrafluoropropyl) diisopropylamide, phosphoric acid bis(2,2,3,3,3-pentafluoropropyl) N-isopropylmethylamide, phosphoric acid bis(2,2,3,3,3-pentafluoropropyl) diisopropylamide, phosphoric acid bis(2,2,3,3,4,4,5,5-octafluoropentyl) N-isopropylmethylamide, phosphoric acid bis(2,2,3,3,4,4,5,5-octafluoropentyl) diisopropylamide, phosphoric acid bis(2,2,3,3,4,4,5,5,6,6,7,7-dodecafluoroheptyl) N-isopropylmethylamide, phosphoric acid bis(2,2,3,3,4,4,5,5,6,6,7,7-dodecafluoroheptyl) diisopropylamide, phosphoric acid 2,2,3,3-tetrafluoropropyl 2,2,2-trifluoroethyl N-isopropylmethylamide, and phosphoric acid 2,2,3,3-tetrafluoropropyl 2,2,2-trifluoroethyl diisopropylamide.

Examples of the fluorine-containing phosphate ester-amide in which $R^1$ and $R^2$ are bonded together to form a four- to eight-membered cyclic structure may include phosphoric acid bis(2,2,2-trifluoroethyl)2-methylpyrrolidide, phosphoric acid bis(2,2,2-trifluoroethyl)2,5-dimethylpyrrolidide, phosphoric acid bis(2,2,2-trifluoroethyl)2-methylpiperidide, phosphoric acid bis(2,2,2-trifluoroethyl)2-ethylpiperidide, phosphoric acid bis(2,2,2-trifluoroethyl)2,2-dimethylpiperidide, phosphoric acid bis(2,2,2-trifluoroethyl)2,6-dimethylpiperidide, phosphoric acid bis(2,2,2-trifluoroethyl)2,2,6-trimethylpiperidide, phosphoric acid bis(2,2,2-trifluoroethyl)2,2,6,6-tetramethylpiperidide, phosphoric acid bis(2,2,2-trifluoroethyl)2-methylmorpholide, phosphoric acid bis(2,2,2-trifluoroethyl) 2,6-dimethylmorpholide, phosphoric acid bis(2,2,2-trifluoroethyl)2,2,6,6-tetramethylmorpholide, phosphoric acid bis(2,2,2-trifluoroethyl)2-methylpiperazide, phosphoric acid bis(2,2,2-trifluoroethyl)2,6-dimethylpiperazide, phosphoric acid bis(2,2,2-trifluoroethyl)2,2,6,6-tetramethylpiperazide, phosphoric acid bis(2,2,2-trifluoroethyl)N'-methyl-2-methylpiperazide, phosphoric acid bis(2,2,2-trifluoroethyl)N'-methyl-2,6-dimethylpiperazide, phosphoric acid bis(2,2,2-trifluoroethyl)N'-methyl-2,2,6,6-tetramethylpiperazide, phosphoric acid bis(2,2,3,3-tetrafluoropropyl)2-methylpiperidide, phosphoric acid bis(2,2,3,3,3-pentafluoropropyl)2-methylpiperidide, phosphoric acid bis(2,2,3,3,4,4,5,5-octafluoropentyl)2-methylpiperidide, phosphoric acid bis(2,2,3,3,4,4,5,5,6,6,7,7-dodecafluoroheptyl)2-methylpiperidide, phosphoric acid bis(2,2,3,3,4,4,5,5,6,6,7,7-dodecafluoroheptyl)2,2,6,6-tetramethylpiperidide, and phosphoric acid 2,2,3,3-tetrafluoropropyl 2,2,2-trifluoroethyl 2-methylpiperidide.

When the amide nitrogen atom in the fluorine-containing phosphate ester-amide of the present invention is bonded to two secondary or tertiary carbons as shown in the general formula (2) above, the fluorine-containing phosphate ester-amide has further improved hydrolysis resistance. Examples of the fluorine-containing phosphate ester-amide represented by the general formula (2) may include phosphoric acid bis(2,2,2-trifluoroethyl) diisopropylamide, phosphoric acid bis(2,2,2-trifluoroethyl) N-isopropylcyclohexylamide, phosphoric acid bis(2,2,2-trifluoroethyl) N-isopropylcyclooctylamide, phosphoric acid bis(2,2,2-trifluoroethyl) N-(2-methoxy-1-methylethyl)isopropylamide, phosphoric acid bis(2,2,2-trifluoroethyl) N-(2-hydroxy-1-methylethyl)isopropylamide, phosphoric acid bis(2,2,2-trifluoroethyl) N-(2-amino-1-methylethyl)isopropylamide, phosphoric acid bis(2,2,2-trifluoroethyl) N-[2-(methylamino)-1-methylethyl]isopropylamide, phosphoric acid bis(2,2,2-trifluoroethyl) N-[2-(dimethylamino)-1-methylethyl]isopropylamide, phosphoric acid bis(2,2,2-trifluoroethyl) N-sec-butylisopropylamide, phosphoric acid bis(2,2,2-trifluoroethyl) di-sec-butylamide, phosphoric acid bis(2,2,2-trifluoroethyl) N-sec-butyl-t-butylamide, phosphoric acid bis(2,2,2-trifluoroethyl) N-t-butylisopropylamide, phosphoric acid bis(2,2,2-trifluoroethyl) di-t-butylamide, phosphoric acid bis(2,2,2-trifluoroethyl) N-t-amylisopropylamide, phosphoric acid bis(2,2-difluoroethyl) diisopropylamide, phosphoric acid bis(2,2,3,3-tetrafluoropropyl) diisopropylamide, phosphoric acid bis(2,2,3,3,3-pentafluoropropyl) diisopropylamide, phosphoric acid bis(2,2,3,3,4,4,5,5-octafluoropentyl) diisopropylamide, phosphoric acid bis(2,2,3,3,4,4,5,5,6,6,7,7-dodecafluoroheptyl) diisopropylamide, phosphoric acid 2,2,3,3-tetrafluoropropyl 2,2,2-trifluoroethyl diisopropylamide, phosphoric acid bis(2,2,2-trifluoroethyl) 2,6-dimethylpyrrolidide, phosphoric acid bis(2,2,2-trifluoroethyl) 2,6-dimethylpiperidide, phosphoric acid bis(2,2,2-trifluoroethyl) 2,2,6-trimethylpiperidide, phosphoric acid bis(2,2,2-trifluoroethyl) 2,2,6,6-tetramethylpiperidide, phosphoric acid bis(2,2,2-trifluoroethyl) 2,6-dimethylmorpholide, phosphoric acid bis(2,2,2-trifluoroethyl) 2,2,6,6-tetramethylmorpholide, phosphoric acid bis(2,2,2-trifluoroethyl) 2,6-dimethylpiperazide, phosphoric acid bis(2,2,2-trifluoroethyl) 2,2,6,6-tetramethylpiperazide, phosphoric acid bis(2,2,2-trifluoroethyl) N'-methyl-2,6-dimethylpiperazide, phosphoric acid bis(2,2,2-trifluoroethyl) N'-methyl-2,2,6,6-tetramethylpiperazide, phosphoric acid bis(2,2,3,3-tetrafluoropropyl) 2,6-dimethylpiperidide, phosphoric acid bis(2,2,3,3,3-pentafluoropropyl) 2,6-dimethylpiperidide, phosphoric acid bis(2,2,3,3,4,4,5,5-octafluoropentyl) 2,6-dimethylpiperidide, phosphoric acid bis(2,2,3,3,4,4,5,5,6,6,7,7-dodecafluoroheptyl) 2,6-dimethylpiperidide, and phosphoric acid 2,2,3,3-tetrafluoropropyl 2,2,2-trifluoroethyl 2,6-dimethylpiperidide.

The fluorine-containing phosphate ester-amide of the present invention that is represented by the general formula (1) or (2) can be synthesized according to a method shown in, for example, Non-Patent Literature 3. Specifically, the fluorine-containing phosphate ester-amide can be synthesized by reacting a secondary amine (6) with a fluorine-containing chlorophosphate (5) derived from phosphorus trichloride and a fluorine-containing alcohol, as shown in scheme (3).

[Chemical formula 3]

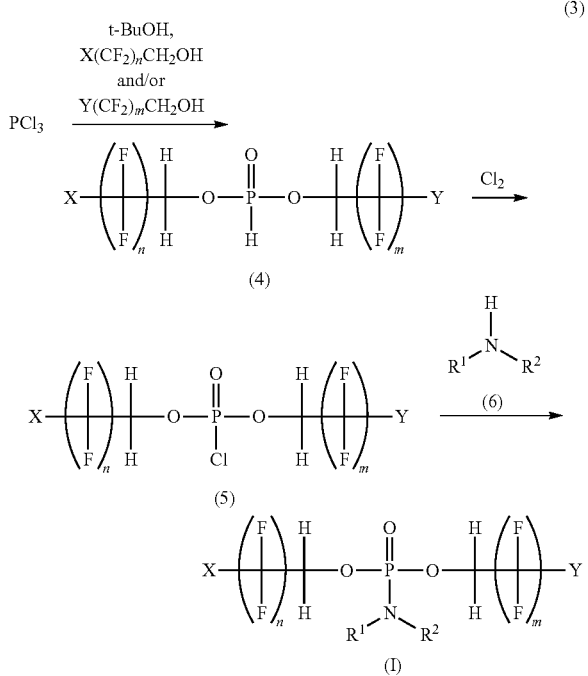

The obtained crude product of the fluorine-containing phosphate ester-amide can be used for flame retardant applications without any treatment. However, the crude product can be purified by a known method such as an extraction method, a distillation method, or a recrystallization method. In this case, the contents of moisture, phosphoric acid, condensation products and chloride of phosphoric acid, the raw material amine, the raw material alcohol, and the intermediate fluorine-containing chlorophosphate that are present as impurities can be lowered, or the contents of the impurities can be reduced to substantially zero.

The use of the fluorine-containing phosphate ester-amide of the present invention will next be described. The fluorine-containing phosphate ester-amide of the present invention has high flame retardancy, i.e., has no flash point, and also has much superior hydrolysis resistance, i.e., is stable not only under neutral conditions but also under acidic or alkaline conditions. As for physical properties, the fluorine-containing phosphate ester-amide has a high boiling point and a low freezing point, so that the temperature range of its liquid state is wide. The fluorine-containing phosphate ester-amide also has features such as a relatively high dielectric constant and therefore can be used alone or as a mixture with a material for various applications.

When the fluorine-containing phosphate ester-amide of the present invention is added to a resin, flame retardancy can be imparted to the resin. Particularly, since the fluorine-containing phosphate ester-amide of the present invention has high flame retardancy and hydrolysis resistance, the flame retardancy can be imparted to the resin by adding only a small amount of the fluorine-containing phosphate ester-amide, and the imparted flame retardancy can be maintained for a long time.

Examples of the method of adding the fluorine-containing phosphate ester-amide to the resin may include: a method in which the fluorine-containing phosphate ester-amide is added to a raw material monomer before the resin is synthesized and then the monomer is polymerized; and a method in which the fluorine-containing phosphate ester-amide is mixed by a known kneading method when the resin is molded. Examples of the resin to which flame retardancy is imparted include: thermoplastic resins such as polyethylene resins and polyester resins; and thermosetting resins such as polyurethane resins and phenolic resins. The amount of the fluorine-containing phosphate ester added to any of these resins is 2 to 20% by weight with respect to the weight of the resin. An amount added of less than 2% is not preferred because flame retardancy is not sufficient. An amount added of more than 20% is not preferred because influences on the properties of the resin increase.

The fluorine-containing phosphate ester-amide of the present invention may be added to a flammable liquid and used to impart flame retardancy to the flammable liquid, i.e., to eliminate or raise its flash point or to impart self-extinguishing properties so that combustion does not continue when the flammable liquid is ignited. Since the fluorine-containing phosphate ester-amide of the present invention has very high compatibility with organic compounds, the fluorine-containing phosphate ester-amide can be mixed with various flammable liquids. The flammable liquid to which flame retardancy is imparted may be any of flammable liquids used as solvents for organic synthesis, secondary battery electrolytes, extractants, washing agents, etc. Examples of the flammable liquid may include: hydrocarbons such as heptane, dodecane, toluene, and ethylbenzene; halogenated hydrocarbons such as dichloroethane and chlorobenzene; alcohols such as ethanol, 1-butanol, 1-octanol, ethylene glycol, and glycerin; ethers such as diisopropyl ether, di-n-butyl ether, and tetrahydrofuran; ketones such as methyl ethyl ketone and cyclohexanone; carboxylic acids such as acetic acid and 2-ethylhexanoic acid; esters such as butyl acetate, diethyl succinate, and diethyl phthalate; lactones such as γ-butyrolactone; carbonates such as dimethyl carbonate, diethyl carbonate, ethyl methyl carbonate, ethylene carbonate, and propylene carbonate; amines such as tri-n-butylamine and N,N-dimethylaniline; amides such as N,N-dimethylformamide, N-methylpyrrolidone, and 1,3-dimethylimidazolidinone; sulfides such as di-n-butylsulfide; sulfoxides such as dimethyl sulfoxide; and phosphate esters such as triethyl phosphate and tri-n-butyl phosphate. The amount of the fluorine-containing phosphate ester added to any of the above flammable liquids varies depending on the type and application of the flammable liquid, but the volume ratio of the fluorine-containing phosphate ester-amide to the flammable liquid is generally 0.1 to 10.

Among the flame retardant liquids to which flame retardancy is imparted by addition of the fluorine-containing phosphate ester-amide of the present invention, a non-flammable liquid with no flash point is highly advantageous because its safety is higher and restrictions imposed on a facility for handling the liquid can be reduced. When the boiling point of the fluorine-containing phosphate ester-amide added to a flammable liquid is low, the flash point can be eliminated with a relatively small amount of addition, and this is particularly effective.

The fluorine-containing phosphate ester-amide of the present invention or a flame retardant liquid containing the same can be used as a solvent for organic synthesis. Examples of the organic synthesis reaction may include esterification reactions, etherification reactions, amidation reactions, amination reactions, hydrolysis reactions, cross-coupling reactions, oxidation reactions, reduction reactions, halogenation reactions, and polymerization reactions.

The fluorine-containing phosphate ester-amide of the present invention is excellent in hydrolysis resistance and is therefore very effective as a solvent for safely performing a reaction in coexistence with water, a reaction in which water is generated during the reaction, a hydrolysis reaction, etc. The fluorine-containing phosphate ester-amide of the present invention has high flame retardancy, also has high resistance to oxidation, and is therefore particularly effective as a solvent for performing an oxidation reaction industrially safely. The reaction conditions vary depending on the type of the reaction. Since the fluorine-containing phosphate ester of the present invention has a low melting point and high thermal stability, the reaction can be performed in a wide temperature range of −30 to 200° C.

If necessary, after the reaction, the reaction solution may be brought into contact with water to remove unreacted water-soluble raw materials, a water-soluble product, a water-soluble catalyst, etc. In this case, the extraction conditions are not limited because the fluorine-containing phosphate ester of the present invention is stable against hydrolysis under any of acidic, neutral, and basic conditions. The product can be separated from the solution containing the fluorine-containing phosphate ester-amide by a crystallization method, a distillation method, etc. The fluorine-containing phosphate ester-amide of the present invention has a relatively high boiling point. Therefore, when the target product is a low-boiling point component, the distillation method is particularly effective because the process is simple.

The fluorine-containing phosphate ester-amide of the present invention not only has high compatibility with flammable liquids but also can dissolve salts such as electrolyte salts. Therefore, the fluorine-containing phosphate ester-amide of the present invention or a flame retardant liquid containing the same can be used as a solvent for secondary battery electrolytes. Examples of the secondary batteries may include lithium ion secondary batteries, lithium-air batteries, magnesium ion secondary batteries, sodium ion secondary batteries, and aluminum ion secondary batteries. Particularly, in metal-air batteries such as lithium-air batteries that use air as the positive electrode, moisture absorption due to contact with outside air can easily cause hydrolysis of electrolytes contents. Therefore, the use of the fluorine-containing phosphate ester-amide of the present invention having high hydrolysis resistance or a flame retardant liquid containing the same as a solvent is very effective.

The fluorine-containing phosphate ester-amide of the present invention or a flame retardant liquid containing the same can be used for, in addition to the above-described applications, applications such as flame retardant hydraulic fluids, flame retardant lubricants, flame retardant extractants, and flame retardant cleaning agents which are on the basis of the physical features of the fluorine-containing phosphate ester-amide such as high flame retardancy, hydrolysis resistance, and a wide temperature range in which the fluorine-containing phosphate ester-amide is liquid.

EXAMPLES

The present invention will next be described in detail by way of Examples. However, the present invention is not limited to these Examples.

Example 1

Synthesis of phosphoric acid bis(2,2,2-trifluoroethyl) diisopropylamide (BTFDIA)

[Chemical formula 4]

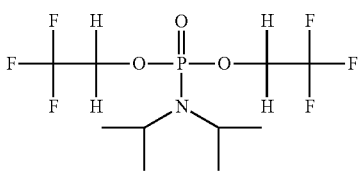

A four-necked flask equipped with a stirrer was charged with 832 g of chloroform and 447 g of bis(2,2,2-trifluoroethyl) chlorophosphate (purity: 90.3%), and the mixture was cooled to 0° C. in an ice-salt bath. 334 g of diisopropylamine was added dropwise to the mixture under stirring over 3 hours using a dropping funnel while reaction temperature was controlled to 0 to 5° C. After completion of the dropwise addition, the temperature was returned to room temperature, and the stirring was continued for 12 hours. After completion of the reaction, 2,500 g of a 5% aqueous sodium hydrogencarbonate solution was added. Then the mixture was stirred, and the organic layer was separated. After chloroform was removed from the organic layer by evaporation, a fraction with a boiling point of 80° C./0.8 kPa was separated by distillation to thereby obtain 432 g of a colorless liquid.

NMR analysis and GC-MS analysis were performed, and the obtained liquid was confirmed to be phosphoric acid bis(2,2,2-trifluoroethyl) diisopropylamide.

$^1$H-NMR (CDCl$_3$, TMS)

δ 4.20-4.35 (m, 4H), 3.41-3.56 (m, 2H), 1.25 (d, J=4 Hz, 12H) $^{13}$C-NMR (CDCl$_3$, TMS)

δ 122.88 (dq, J=12 Hz, 278 Hz), 62.50 (dq, J=4 Hz, 38 Hz), 46.70 (d, J=5 Hz), 22.30 (d, J=1 Hz)

$^{19}$F-NMR (CDCl$_3$, CFCl$_3$)

δ -75.76 (t, J=9 Hz)

GC-MS (EI)

m/z 330 [M-CH$_3$]$^+$, 302, 288, 268, 242, 188, 162, 142, 108, 84, 43

Example 2

Synthesis of phosphoric acid bis(2,2,2-trifluoroethyl) N-isopropyl-n-propylamide (BTFINA)

[Chemical formula 5]

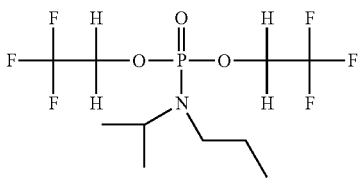

A four-necked flask equipped with a stirrer was charged with 83 g of chloroform and 45 g of bis(2,2,2-trifluoroethyl) chlorophosphate (purity: 90.3%), and the mixture was cooled to 0° C. in an ice-salt bath. 33 g of N-isopropyl-n-propylamine was added dropwise to the mixture under stirring over 2 hours using a dropping funnel while reaction temperature was controlled to 0 to 5° C. After completion of the dropwise addition, the temperature was returned to room temperature, and the stirring was continued for 12 hours. After completion of the reaction, 250 g of a 5% aqueous sodium hydrogencarbonate solution was added. Then the mixture was stirred, and the organic layer was separated. After chloroform was removed from the organic layer by evaporation, a fraction with a boiling point of 82° C./0.8 kPa was separated by distillation to thereby obtain 41 g of a colorless liquid.

NMR analysis and GC-MS analysis were performed, and the obtained liquid was confirmed to be phosphoric acid bis(2,2,2-trifluoroethyl) N-isopropyl-n-propylamide.

$^1$H-NMR (CDCl$_3$, TMS)

δ 4.20-4.35 (m, 4H), 3.41-3.56 (m, 1H), 2.95-2.87 (m, 2H), 1.63-1.53 (m, 2H, J=8 Hz), 1.25 (d, J=4 Hz, 6H) 0.88 (t, 3H, J=8 Hz)

$^{19}$F-NMR (CDCl$_3$, CFCl$_3$)

δ -75.74 (t, J=9 Hz)

GC-MS (EI)

m/z 330 [M-CH$_3$]$^+$, 315, 302, 288, 274, 246, 225, 204, 163, 135, 108, 84, 56, 43

Example 3

Synthesis of phosphoric acid bis(2,2,2-trifluoroethyl) 2-methylpiperidide (BTFMPI)

[Chemical formula 6]

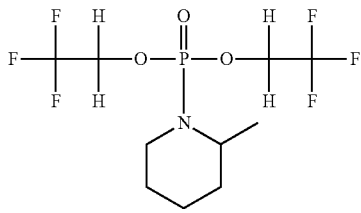

A four-necked flask equipped with a stirrer was charged with 119 g of chloroform and 22.6 g of bis(2,2,2-trifluoroethyl) chlorophosphate (purity: 90.3%), and the mixture was cooled to 0° C. in an ice-salt bath. 17.5 g of 2-methylpiperidine was added dropwise to the mixture under stirring over 3 hours using a dropping funnel while reaction temperature was controlled to 0 to 5° C. After completion of the dropwise addition, the temperature was returned to room temperature, and the stirring was continued for 12 hours. After completion of the reaction, 300 g of a 2.5% aqueous sodium hydrogencarbonate solution was added. Then the mixture was stirred, and the organic layer was separated. After chloroform was removed from the organic layer by evaporation, a fraction with a boiling point of 78° C./0.4 kPa was separated by distillation to thereby obtain 23 g of a colorless liquid.

NMR analysis and GC-MS analysis were performed, and the obtained liquid was confirmed to be phosphoric acid bis(2,2,2-trifluoroethyl) 2-methylpiperidide.

$^1$H-NMR (CDCl$_3$, TMS)

δ 4.23-4.33 (m, 4H), 3.81-3.87 (m, 1H), 3.28-3.33 (m, 1H), 2.96-3.06 (m, 1H), 1.60-1.70 (m, 4H), 1.36-1.53 (m, 2H), 1.24 (d, 3H, J=8 Hz)

$^{13}$C-NMR (CDCl$_3$, TMS)

δ 122.79 (dd, J=11, 278 Hz), 62.91 (dq, J=5 Hz, 37 Hz), 62.75 (dq, J=5 Hz, 38 Hz), 47.45 (d, J=3 Hz), 39.35 (d, J=3 Hz), 30.52 (d, J=4 Hz), 25.90 (d, J=4 Hz), 18.63 (s), 16.50 (d, J=2 Hz)

$^{19}$F-NMR (CDCl$_3$, CFCl$_3$)

δ -75.76 (t, 8 Hz), -75.79 (t, 8 Hz)

GC-MS (ET)

m/z 328 [M-CH$_3$]$^+$, 300, 274, 245, 174, 163, 97, 83, 55, 41

Example 4

Synthesis of phosphoric acid bis(2,2,2-trifluoroethyl) N-t-butylmethylamide (BTFTBMA)

[Chemical formula 7]

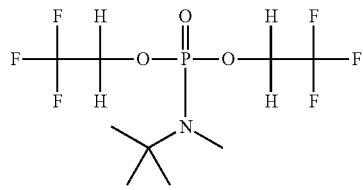

A four-necked flask equipped with a stirrer was charged with 120 g of chloroform, 48 g of bis(2,2,2-trifluoroethyl) chlorophosphate (purity: 90.3%), and 19 g of triethylamine, and the mixture was cooled to 0° C. in an ice-salt bath. 14 g of N-t-butylmethylamine was added dropwise to the mixture under stirring over 2 hours using a dropping funnel while reaction temperature was controlled to 0 to 5° C. After completion of the dropwise addition, the temperature was returned to room temperature, and the stirring was continued for 12 hours. After completion of the reaction, 250 g of a 2.5% aqueous sodium hydrogencarbonate solution was added. Then the mixture was stirred, and the organic layer was separated. After chloroform was removed from the organic layer by evaporation, a fraction with a boiling point of 59° C./0.1 kPa was separated by distillation to thereby obtain 36 g of a colorless liquid.

NMR analysis and GC-MS analysis were performed, and the obtained liquid was confirmed to be phosphoric acid bis(2,2,2-trifluoroethyl) N-t-butylmethylamide.

$^1$H-NMR (CDCl$_3$, TMS)

δ 4.33-4.25 (m, 4H), 2.74 (d, 3H, J=10), 1.34 (s, 9H)

$^{13}$C-NMR (CDCl$_3$, TMS)

δ 123.12 (dq, J=11 Hz, 277 Hz), 62.81 (dq, J=5 Hz, 38 Hz), 55.69 (d, J=3 Hz), 31.20 (d, J=4 Hz), 28.91 (d, J=4 Hz)

$^{19}$F-NMR (CDCl$_3$, CFCl$_3$)

δ −75.60 (t, J=8 Hz)

GC-MS (EI)

m/z 316 [M-CH$_3$]$^+$, 274, 256, 216, 176, 118, 96, 83, 70, 56, 42, 30

Example 5

Synthesis of phosphoric acid bis(2,2,3,3-tetrafluoropropyl) diisopropylamide (BTPDIA)

[Chemical formula 8]

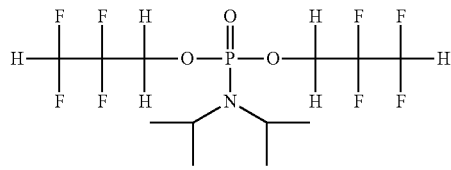

A four-necked flask equipped with a stirrer was charged with 120 g of chloroform and 54 g of bis(2,2,3,3-tetrafluoropropyl) chlorophosphate (purity: 93.9%), and the mixture was cooled to 0° C. in an ice-salt bath. 33 g of diisopropylamine was added dropwise to the mixture under stirring over 2 hours using a dropping funnel while reaction temperature was controlled to 0 to 5° C. After completion of the dropwise addition, the temperature was returned to room temperature, and the stirring was continued for 12 hours. After completion of the reaction, 250 g of a 2.5% aqueous sodium hydrogencarbonate solution was added. Then the mixture was stirred, and the organic layer was separated. After chloroform was removed from the organic layer by evaporation, a fraction with a boiling point of 105° C./0.2 kPa was separated by distillation to thereby obtain 44 g of a colorless liquid.

NMR analysis and GC-MS analysis were performed, and the obtained liquid was confirmed to be phosphoric acid bis(2,2,3,3-tetrafluoropropyl) diisopropylamide.

$^1$H-NMR (CDCl$_3$, TMS)

δ 5.92 (tt, 1H, J=3 Hz, 47 Hz), 4.39-4.51 (m, 4H), 3.42-3.57 (m, 2H), 1.26 (d, J=4 Hz, 12H)

$^{19}$F-NMR (CDCl$_3$, CFCl$_3$)

δ −137.97 (d, 2F, J=47 Hz), −125.15 (dt, 2F, J=3 Hz, 13 Hz)

GC-MS (EI)

m/z 394 [M-CH$_3$]$^+$, 379

Example 6

Synthesis of phosphoric acid bis(2,2,2-trifluoroethyl) N-isopropyl-2-methoxyethylamide (BTFIMEA)

[Chemical formula 9]

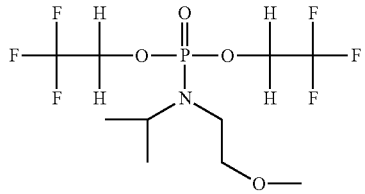

A four-necked flask equipped with a stirrer was charged with 150 g of chloroform, 38 g of bis(2,2,2-trifluoroethyl) chlorophosphate (purity: 90.3%), and 15 g of triethylamine, and the mixture was cooled to 0° C. in an ice-salt bath. 14 g of N-isopropyl-2-methoxyethylamine was added dropwise to the mixture under stirring over 2 hours using a dropping funnel while reaction temperature was controlled to 0 to 5° C. After completion of the dropwise addition, the temperature was returned to room temperature, and the stirring was continued for 15 hours. After completion of the reaction, 200 g of a 2.5% aqueous sodium hydrogencarbonate solution was added. Then the mixture was stirred, and the organic layer was separated. After chloroform was removed from the organic layer by evaporation, a fraction with a boiling point of 75° C./0.1 kPa was separated by distillation to thereby obtain 32 g of a colorless liquid.

NMR analysis and GC-MS analysis were performed, and the obtained liquid was confirmed to be phosphoric acid bis(2,2,2-trifluoroethyl) N-isopropyl-2-methoxyethylamide.

$^1$H-NMR (CDCl$_3$, TMS)

δ 4.38-4.28 (m, 4H), 3.70-3.60 (m, 1H), 3.46 (t, J=8 Hz, 2H), 3.35 (s), 3.21 (td, J=6 Hz, 14 Hz, 2H), 1.21 (d, 7 Hz, 6H)

$^{13}$C-NMR (CDCl$_3$, TMS)
δ 123.10 (dq, J=11 Hz, 277 Hz), 72.24 (s), 62.92 (dq, J=4 Hz, 38 Hz), 58.74 (s), 49.32 (d, J=4 Hz), 42.63 (d, J=5 Hz), 21.60 (d, J=3 Hz)
$^{19}$F-NMR (CDCl$_3$, CFCl$_3$)
δ −75.71 (t, J=8 Hz)
GC-MS (EI)
m/z 346 [M-CH$_3$]$^+$, 316, 300, 288, 274, 220, 163, 70, 59, 55, 44, 43

Examples 7 to 12

Values of Physical Properties of Fluorine-Containing Phosphate Ester-Amides

The flash point of each of the fluorine-containing phosphate ester-amides obtained in Examples 1 to 6 was measured using a Seta-type flash point measuring device (type RT-1, manufactured by Yoshida Kagaku Kikai Co. Ltd.). Their viscosity at 20° C. was measured using a cone-plate viscometer (type DV-1PRIME, manufactured by Brook-Field). Moreover, their freezing point was measured according to a method in JIS K0065. The results are shown in TABLE 1.

TABLE 1

| | FLAME RETARDANT | FLASH POINT (° C.) | VISCOSITY (mPa · s) | FREEZING POINT (° C.) |
|---|---|---|---|---|
| EXAMPLE 7 | BTFDIA | NOT IGNITED | 8.6 | <−30 |
| EXAMPLE 8 | BTFINA | NOT IGNITED | 8.3 | <−30 |
| EXAMPLE 9 | BTFMPI | NOT IGNITED | 19.6 | <−30 |
| EXAMPLE 10 | BTFTBMA | NOT IGNITED | 7.3 | 9 |
| EXAMPLE 11 | BTPDIA | NOT IGNITED | 42.4 | <−30 |
| EXAMPLE 12 | BTFIMEA | NOT IGNITED | 11.6 | <−30 |

As can be seen from TABLE 1, BTFDIA, BTFINA, BTFMPI, BTFTBMA, BTPDIA, and BTFIMEA, which are the fluorine-containing phosphate ester-amides of the present invention, are all characterized in that they have no flash point, are non-flammable, have high safety, and have a high boiling point and a low freezing point, so that the temperature range of their liquid state is wide.

Examples 13 to 18 and Comparative Examples 1 to 4

Hydrolysis Resistance Test on Phosphate Esters (Neutral Conditions)

A glass pressure container was charged with 2.0 g of a phosphate ester, 8.0 g of γ-butyrolactone, and 0.5 g of water and was hermetically sealed, and the mixture was heated at 125° C. in an oil bath for 250 hours. After heating, the test solution was analyzed by GC and $^1$H-NMR, and the rate of hydrolysis was computed using the following formula.

Rate of hydrolysis/%=(hydrolyzed phosphate ester/moles)/[(phosphate ester/moles)+(hydrolyzed phosphate ester/moles)]×100

In Example 13, BTFDIA obtained in Example 1 was used as the phosphate ester. In Example 14, BTFINA obtained in Example 2 was used as the phosphate ester. In Example 15, BTFMPI obtained in Example 3 was used as the phosphate ester. In Example 16, BTFTBMA obtained in Example 4 was used as the phosphate ester. In Example 17, BTPDIA obtained in Example 5 was used as the phosphate ester. In Example 18, BTFIMEA obtained in Example 6 was used as the phosphate ester. In Comparative Examples 1 to 4, conventionally known phosphoric acid bis(2,2,2-trifluoroethyl)dimethylamide, phosphoric acid bis(2,2,2-trifluoroethyl)diethylamide, phosphoric acid tris(2,2,2-trifluoroethyl)ester, and trimethyl phosphate, respectively, were used as the phosphate esters. The results are shown in TABLE 2.

TABLE 2

| | PHOSPHATE ESTER | RATE OF HYDROLYSIS (%) |
|---|---|---|
| EXAMPLE 13 | BTFDIA | 0 |
| EXAMPLE 14 | BTFINA | 5 |
| EXAMPLE 15 | BTFMPI | 7 |
| EXAMPLE 16 | BTFTBMA | 5 |
| EXAMPLE 17 | BTPDIA | 1 |
| EXAMPLE 18 | BTFIMEA | 6 |
| COMPARATIVE EXAMPLE 1 | PHOSPHORIC ACID BIS(2,2,2-TRIFLUOROETHYL)-DIMETHYLAMIDE | 100 |
| COMPARATIVE EXAMPLE 2 | PHOSPHORIC ACID BIS(2,2,2-TRIFLUOROETHYL)-DIETHYLAMIDE | 88 |
| COMPARATIVE EXAMPLE 3 | PHOSPHORIC ACID TRIS(2,2,2-TRIFLUOROETHYL)-ESTER | 100 |
| COMPARATIVE EXAMPLE 4 | TRIMETHYL PHOSPHATE | 100 |

As is clear from TABLE 2, BTFDIA, BTFINA, BTFMPI, BTFBMA, BTPDIA, and BTFIMEA, which are the fluorine-containing phosphate ester-amides of the present invention, have significantly better hydrolysis resistance than that of the conventionally known phosphate esters.

Examples 19 to 24 and Comparative Examples 5 to 8

Hydrolysis Resistance Test in Phosphate Esters (Basic Conditions and Acidic Conditions)

A glass pressure container was charged with 2.0 g of a phosphate ester and 2.0 g of a 1 mol/L aqueous potassium hydroxide solution and was hermetically sealed, and the mixture was heated at 85° C. under stirring in an oil bath for 50 hours. After heating, the test solution was analyzed by GC and $^1$H-NMR, and the rate of hydrolysis was computed using the following formula.

Rate of hydrolysis/%=(hydrolyzed phosphate ester/moles)/[(phosphate ester/moles)+(hydrolyzed phosphate ester/moles)]×100

Separately, a glass pressure container was charged with 2.0 g of the phosphate ester and 2.0 g of a 1 mol/L aqueous sulfuric acid solution and was hermetically sealed, and the mixture was heated at 85° C. under stirring in an oil bath for 50 hours. After heating, the test solution was analyzed by GC and $^1$H-NMR, and the rate of hydrolysis was computed using the following formula.

Rate of hydrolysis/%=(hydrolyzed phosphate ester/moles)/[(phosphate ester/moles)+(hydrolyzed phosphate ester/moles)]×100

In Example 19, BTFDIA obtained in Example 1 was used as the phosphate ester. In Example 20, BTFINA obtained in Example 2 was used as the phosphate ester. In Example 21, BTFMPI obtained in Example 3 was used as the phosphate ester. In Example 22, BTFTBMA obtained in Example 4 was used as the phosphate ester. In Example 23, BTPDIA obtained in Example 5 was used as the phosphate ester. In Example 24, BTFIMEA obtained in Example 6 was used as the phosphate ester. In Comparative Examples 5 to 8, conventionally known phosphoric acid bis(2,2,2-trifluoroethyl)dimethylamide, phosphoric acid tris(2,2,2-trifluoroethyl)ester, trimethyl phosphate, and triethyl phosphate, respectively, were used as the phosphate esters. The results are shown in TABLE 3.

TABLE 3

| | PHOSPHATE ESTER | RATE OF HYDROLYSIS (%) | |
|---|---|---|---|
| | | 1 mol/L AQUEOUS KOH | 1 mol/L AQUEOUS H2SO4 |
| EXAMPLE 19 | BTFDIA | 0 | 0 |
| EXAMPLE 20 | BTFINA | 5 | 2 |
| EXAMPLE 21 | BTFMPI | 12 | 3 |
| EXAMPLE 22 | BTFTBMA | 7 | 5 |
| EXAMPLE 23 | BTPDIA | 2 | 1 |
| EXAMPLE 24 | BTFIMEA | 6 | 5 |
| COMPARATIVE EXAMPLE 5 | PHOSPHORIC ACID BIS(2,2,2-TRIFLUOROETHYL)-DIMETHYLAMIDE | 100 | 9 |
| COMPARATIVE EXAMPLE 6 | PHOSPHORIC ACID TRIS(2,2,2-TRI-FLUOROETHYL)-ESTER | 100 | 100 |

TABLE 3-continued

| | PHOSPHATE ESTER | RATE OF HYDROLYSIS (%) | |
|---|---|---|---|
| | | 1 mol/L AQUEOUS KOH | 1 mol/L AQUEOUS H2SO4 |
| COMPARATIVE EXAMPLE 7 | TRIMETHYL PHOSPHATE | 100 | 34 |
| COMPARATIVE EXAMPLE 8 | TRIETHYL PHOSPHATE | 100 | 8 |

As can be seen from TABLE 3, BTFDIA, BTFINA, BTFMPI, BTFTBMA, BTPDIA, and BTFIMEA, which are the fluorine-containing phosphate ester-amides of the present invention, have much superior hydrolysis resistance under both the basic and acidic conditions. However, phosphoric acid bis(2,2,2-trifluoroethyl)dimethylamide, phosphoric acid tris(2,2,2-trifluoroethyl)ester, trimethyl phosphate, and triethyl phosphate, which are conventionally known fluorine-containing phosphate esters, do not have sufficient hydrolysis resistance under one of or both the basic and acidic conditions.

Examples 25 to 27 and Comparative Examples 9 to 11

Examples of Flame Retardation of Urethane Resins

A flask was charged with 100 g of polyol (product name: MN-3050ONE, manufactured by Mitsui Chemicals, Inc.), 1.2 g of silicon oil (product name: L-520, manufactured by Nippon Unicar Co., Ltd.), 0.25 g of a tin-based catalyst (dibutyltin dilaurate), 0.15 g of an amine-bases catalyst (product name: KAOLIZER No. 1, manufactured by Kao Corporation), 4.5 g of water, 3.0 g of methylene chloride, and a flame retardant (one of amounts shown in TABLE 4). Then, the mixture was stirred for 1 minute to uniformly mix these components. Next, 55 g of diisocyanate (product name: TDI80/20, manufactured by Mitsui Chemicals, Inc.) was added, and the mixture was stirred for 5 seconds. Then the resultant mixture was poured into a container with a square cross section and was foamed immediately. The foam was cured in a furnace at 120° C. for 30 minutes. A specimen was cut from the obtained foam, and a combustion test according to MVSS-302 was performed. The results are shown in TABLE 4.

TABLE 4

| | FLAME RETARDANT | AMOUNT ADDED g | COMBUSTION DISTANCE mm | JUDGMENT |
|---|---|---|---|---|
| EXAMPLE 25 | BTFDIA | 10 | 26 | NON-FLAMMABLE |
| EXAMPLE 26 | BTFMPI | 10 | 28 | NON-FLAMMABLE |
| EXAMPLE 27 | BTFDIA | 10 | 30 | NON-FLAMMABLE |
| COMPARATIVE EXAMPLE 9 | TRIMETHYL PHOSPHATE | 10 | 73 | SELF-EXTINGUISHABLE |
| COMPARATIVE EXAMPLE 10 | TRIMETHYL PHOSPHATE | 20 | 29 | NON-FLAMMABLE |
| COMPARATIVE EXAMPLE 11 | NONE | — | Burned Away | FLAMMABLE |

As can be seen from TABLE 4, with BTFDIA, BTFMPI, and BTPDIA, which are the fluorine-containing phosphate ester-amides of the present invention, flame retardancy can be imparted to the resin with a smaller amount of addition than that necessary when trimethyl phosphate, which is a conventional flame retardant, is used.

Examples 28 to 30 and Comparative Example 12

Long-Term Test of Duration of Flame Retardancy

The urethane resins obtained in Examples 25 to 27 and Comparative Example 10 were cut, and the cut pieces were held at 85° C. and a relative humidity of 85% for 2 weeks during a high-temperature high-humidity test, and then a combustion test according to MVSS-302 was performed. The results are shown in TABLE 5.

TABLE 5

| | FLAME RETARDANT | AMOUNT ADDED g | COMBUSTION DISTANCE mm | JUDGMENT |
|---|---|---|---|---|
| EXAMPLE 28 | BTFDIA | 10 | 25 | NON-FLAMMABLE |
| EXAMPLE 29 | BTFMPI | 10 | 32 | NON-FLAMMABLE |
| EXAMPLE 30 | BTFDIA | 10 | 29 | NON-FLAMMABLE |
| COMPARATIVE EXAMPLE 12 | TRIMETHYL PHOSPHATE | 20 | 51 | SELF-EXTINGUISHABLE |

As can be seen from TABLE 5, since BTFDIA, BTFMPI, and BTPDIA, which are the fluorine-containing phosphate ester-amides of the present invention, have superior hydrolysis resistance, the resins containing these fluorine-containing phosphate ester-amides can maintain the flame retardant effect for a long time. However, the resin containing trimethyl phosphate, which is a conventional flame retardant, is easily hydrolyzed under high-temperature high-humidity conditions, and therefore it is difficult to maintain the flame retardant effect for a long time.

Examples 31 to 36 and Comparative Examples 13 and 14

Dielectric Constant and Donor Number of Fluorine-Containing Phosphate Ester-Amides The dielectric constant of each of the fluorine-containing phosphate ester-amides obtained in Examples 1 to 6 was measured at 25° C. (1 kHz) using an impedance analyzer (type VersaSTAT, manufactured by TOYO Corporation). Their donor number was computed from Si chemical shift values in $^{29}$Si NMR of a $Ph_2Si(OH)_2$ solution mixture according to a method described in J. Organomet. Chem., 108, 153, (1976). In addition, similar measurements were performed on known non-hydrolyzable fluorine-containing flame retardant liquids, i.e., tris(perfluoropropyl)amine (Comparative Example 13) and methyl perfluorohexyl ether (Comparative Example 14). In Comparative Examples 13 and 14, $Ph_2Si(OH)_2$ did not dissolve at all, and therefore the donor number could not be computed. The results are shown in TABLE 6.

As can be seen from TABLE 6, BTFDIA, BTFINA, BTFMPI, BTFTBMA, BTPDIA, and BTFIMEA, which are the fluorine-containing phosphate ester-amides of the present invention, have higher dielectric constants than those of the other fluorine-containing flame retardant liquids and also have intermediate donor properties.

Examples 37 to 39 and Comparative Examples 15 to 23

Compatibility of Fluorine-Containing Phosphate Ester with Organic Compounds and Examples of Flame Retardant Liquid Containing Fluorine-Containing Phosphate Ester-Amide 2 g of one of flammable liquids shown in TABLE 7 was added to 2 g of BTFDIA obtained in Example 1. The mixture was vigorously shaken, and the state of mixing was visually checked. Similarly, the same mixing test was performed using known fluorine-containing flame retardant liquids, i.e., tris(perfluoropropyl)amine and methyl perfluorohexyl ether.

Next, a quartz filter with a diameter of 21 mm was impregnated with 0.1 mL of one of the liquid mixtures. Then a flame of a lighter was brought close to the lower side of the quartz filter and held at a position 25 mm below the quartz filter for 3 seconds, and whether or not combustion continued was examined. The test was performed 3 times. When the fire was extinguished in less than 3 seconds in all the three tests, a circle (good) rating was assigned. When combustion continued for 3 seconds or longer in at least one of the tests, a cross (poor) rating was assigned. In Comparative Examples 21 to 23, the above combustion test was performed on flammable liquids containing no flame retardant. The results are shown in TABLE 7.

TABLE 6

| | COMPOUND | DIELECTRIC CONSTANT | DONOR NUMBER |
|---|---|---|---|
| EXAMPLE 31 | BTFDIA | 11.5 | 22.4 |
| EXAMPLE 32 | BTFINA | 11.2 | 22.7 |
| EXAMPLE 33 | BTFMPI | 10.9 | 21.8 |
| EXAMPLE 34 | BTFTBMA | 11.3 | 22.3 |
| EXAMPLE 35 | BTPDIA | 10.2 | 22.5 |
| EXAMPLE 36 | BTFIMEA | 12.1 | 23.2 |
| COMPARATIVE EXAMPLE 13 | TRIS(PERFLUOROPROPYL)AMINE | 1.8 | NOT COMPUTABLE (NOT SOLUBLE) |
| COMPARATIVE EXAMPLE 14 | METHYL PERFLUOROHEXYL ETHER | 5.9 | NOT COMPUTABLE (NOT SOLUBLE) |

TABLE 7

| | FLAME RETARDANT | FLAMMABLE LIQUID | STATE OF MIXTURE | COMBUSTION TEST |
|---|---|---|---|---|
| EXAMPLE 37 | BTFDIA | 1-BUTANOL | UNIFORM | ○ |
| EXAMPLE 38 | BTFDIA | DODECANE | UNIFORM | ○ |
| EXAMPLE 39 | BTFDIA | PROPYLENE CARBONATE | UNIFORM | ○ |
| COMPARATIVE EXAMPLE 15 | TRIS(PERFLUOROPROPYL)AMINE | 1-BUTANOL | SEPARATED INTO TWO LAYERS | NOT PERFORMABLE |
| COMPARATIVE EXAMPLE 16 | TRIS(PERFLUOROPROPYL)AMINE | DODECANE | SEPARATED INTO TWO LAYERS | NOT PERFORMABLE |
| COMPARATIVE EXAMPLE 17 | TRIS(PERFLUOROPROPYL)AMINE | PROPYLENE CARBONATE | SEPARATED INTO TWO LAYERS | NOT PERFORMABLE |
| COMPARATIVE EXAMPLE 18 | METHYL PERFLUOROHEXYL ETHER | 1-BUTANOL | SEPARATED INTO TWO LAYERS | NOT PERFORMABLE |
| COMPARATIVE EXAMPLE 19 | METHYL PERFLUOROHEXYL ETHER | DODECANE | SEPARATED INTO TWO LAYERS | NOT PERFORMABLE |
| COMPARATIVE EXAMPLE 20 | METHYL PERFLUOROHEXYL ETHER | PROPYLENE CARBONATE | SEPARATED INTO TWO LAYERS | NOT PERFORMABLE |
| COMPARATIVE EXAMPLE 21 | — | 1-BUTANOL | — | X |
| COMPARATIVE EXAMPLE 22 | — | DODECANE | — | X |
| COMPARATIVE EXAMPLE 23 | — | PROPYLENE CARBONATE | — | X |

As can be seen from TABLE 7, the existing fluorine-containing flame retardant liquids, i.e., tris(perfluoropropyl)amine and methyl perfluorohexyl ether, were not uniformly mixed with the examined flammable liquids, and the mixtures were separated into two layers. However, it was found that the fluorine-containing phosphate ester-amide of the present invention, i.e., BTFDIA, was uniformly mixed with each of the flammable liquids. It was also found that self-extinguishing properties were imparted to the flammable liquids to when the fluorine-containing phosphate ester-amide was added.

Examples 40 and 41 and Comparative Example 24

Examples of Non-Flammable Liquid Containing Fluorine-Containing Phosphate Ester-Amide 5 mL of one of the fluorine-containing phosphate ester-amides obtained in Examples 1 and 2 was mixed with 5 mL of 1,3-dimethylimidazolidinone (abbreviation: DMI, boiling point: 226° C., flash point: 107° C.). The flash point of each of the liquid mixtures was measured using a Seta-type flash point measuring device (type RT-1, manufactured by Yoshida Kagaku Kikai Co. Ltd.). Similarly, 5 mL of triethyl phosphate was mixed with 5 mL of 1,3-dimethylimidazolidinone, and the flash point of the mixture was measured. The results are shown in TABLE 8.

TABLE 8

| | LIQUID MIXTURE | FLASH POINT (° C.) |
|---|---|---|
| EXAMPLE 40 | BTFDIA-DMI (1:1) | NOT IGNITED |
| EXAMPLE 41 | BTFINA-DMI (1:1) | NOT IGNITED |
| COMPARATIVE EXAMPLE 24 | TRIETHYL PHOSPHATE-DMI (1:1) | 112° C. |

As shown in TABLE 8, since the fluorine-containing phosphate ester-amides of the present invention have high flame retardancy, the addition of any of the fluorine-containing phosphate ester-amides to DMI, which is a flammable liquid, allows a non-flammable liquid, i.e., a flame retardant liquid with no flash point, to be prepared. However, triethyl phosphate, which is a comparative phosphate ester, has a flash point and is flammable. Therefore, a flash point was observed in its mixture with DMI, and it was difficult to obtain sufficient flame retardancy.

Example 42

Example of Use of Fluorine-containing Phosphate Ester-Amide as Flame Retardant Solvent for Organic Synthesis (Hydrolysis Reaction)

A 100 mL Schlenk tube was charged with 10 mL (12.5 g) of BTFDIA obtained in Example 1 and 10 mL of water. Then 1.3 g of butyl acetate and 0.6 g of NaOH were added, and the mixture was heated to 70° C. and stirred for 2 hours. After the reaction, two layers were separated and analyzed. It was found that the conversion ratio of butyl acetate was 100% and the hydrolysis had reaction proceeded. No hydrolysis of BTFDIA was found.

BTFDIA, which is the fluorine-containing phosphate ester-amide of the present invention, has no flash point, is non-flammable, and has very high stability against hydrolysis. Therefore, when BTFDIA is used as a solvent, an organic synthesis reaction such as hydrolysis involving water can be performed safely.

Example 43

Example of Use of Fluorine-Containing Phosphate Ester-Amide as Flame Retardant Solvent for Organic Synthesis (Cross-Coupling Reaction)

A 100 mL Schlenk tube was charged with 20 mL (25 g) of BTFDIA obtained in Example 1, and then 1.1 of 4-n- propylphenylboronic acid was added thereto and dissolved therein. After replacing the inside air with nitrogen, 0.040 g of triphenylphosphine, 0.97 g of bromobenzene, 0.047 g of dichlorobis(triphenylphosphine)palladium (II), and 4.0 g of cesium carbonate were added under stirring, and the mixture was allowed to react at 80° C. for 4 hours.

After the reaction, the reaction solution was washed with 20 mL of water, and the organic layer (lower layer) was subjected to GC analysis. It was found that the conversion ratio of bromobenzene was 74% and a cross-coupling product, i.e., 4-n-propylbiphenyl, was produced at a selectivity of 99%. No decomposition of BTFDIA was found in the GC analysis.

BTFDIA, which is the fluorine-containing phosphate ester-amide of the present invention, has no flash point and is non-flammable. Therefore, when BTFDIA is used as a solvent, an organic synthesis reaction such as a cross-coupling reaction can be performed more safely.

Example 44

Example of Use of Flame Retardant Liquid Containing Fluorine-Containing Phosphate Ester-Amide as Flame Retardant Solvent for Organic Synthesis (Cross-Coupling Reaction)

A 100 mL Schlenk tube was charged with 10 mL (12.5 g) g of BTFDIA obtained in Example 1 and 10 mL (10.6) g of 1,3-dimethylimidazolidinone (DMI), and then 1.1 of 4-n-propylphenylboronic acid was added thereto and dissolved therein. After replacing the inside air with nitrogen, 0.040 g of triphenylphosphine, 0.97 g of bromobenzene, 0.047 g of dichloro bis(triphenylphosphine)palladium (II), and 4.0 g of cesium carbonate were added under stirring, and the mixture was allowed to react at 80° C. for 4 hours.

After the reaction, the reaction solution was subjected to GC analysis. It was found that the conversion ratio of bromobenzene was 79% and a cross-coupling product, i.e., 4-n-propylbiphenyl, was produced at a selectivity of 99%. No decomposition of BTFDIA was found in the GC analysis.

The mixture of BTFDIA and DMI is a flame retardant liquid (non-flammable liquid) having no flash point, as shown in Example 40. Therefore, when the mixture is used as a solvent, an organic synthesis reaction such as a cross-coupling reaction can be performed more safely.

Example 45

Example of Use of Fluorine-Containing Phosphate Ester-Amide as Flame Retardant Solvent for Organic Synthesis (Oxidation Reaction)

A 20 mL Schlenk tube was charged with 9 mL (11 g) of BTFDIA obtained in Example 1, 0.15 g of benzyl alcohol, and 0.067 g of platinum oxide. Next, a gas bag filled with oxygen gas was connected to the Schlenk tube, and the atmosphere in the system was replaced with the oxygen gas. Then the mixture was allowed to react at 100° C. for 42 hours.

After the reaction, the reaction solution was subjected to GC analysis. It was found that the conversion ratio of benzyl alcohol was 62% and benzaldehyde was produced at a selectivity of 100%. No decomposition of BTFDIA was found in the GC analysis.

BTFDIA, which is the fluorine-containing phosphate ester-amide of the present invention, has high oxidation resistance and is non-flammable. Therefore, when BTFDIA is used as a solvent, a highly dangerous oxidation reaction can be performed safely.

Example 46 and Comparative Examples 25 and 26

Compatibility of Fluorine-Containing Phosphate Ester-Amide with Electrolyte Salt A 50 mL Schlenk tube was charged with 10 mL (12.5 g) of BTFDIA obtained in Example 1, and $LiN(SO_2CF_3)_2$ (LiTFSI) was gradually added thereto under stirring in a thermostatic bath at 25° C. to determine its solubility. The solubility of known non-hydrolyzable fluorine-containing flame retardant liquids, i.e., tris(perfluoropropyl)amine (Comparative Example 25) and methyl perfluorohexyl ether (Comparative Example 26), was also examined by the same method. The results are shown in TABLE 9.

TABLE 9

| | COMPOUND | SOLUBILITY (g/100 g) |
|---|---|---|
| EXAMPLE 46 | BTFDIA | 18 |
| COMPARATIVE EXAMPLE 25 | TRIS(PERFLUOROPROPYL)-AMINE | <1 |
| COMPARATIVE EXAMPLE 26 | METHYL PERFLUOROHEXYL ETHER | <1 |

As can be seen from TABLE 9, BTFDIA, which is the fluorine-containing phosphate ester-amide of the present invention, can dissolve LiTFSI used as an electrolyte salt for lithium ion secondary batteries, lithium-air batteries, etc. at high concentration. Therefore, the fluorine-containing phosphate ester-amide of the present invention or a flame retardant liquid containing the same can be used as an electrolyte solvent for lithium ion secondary batteries, lithium-air batteries, etc.

INDUSTRIAL APPLICABILITY

The fluorine-containing phosphate ester-amide of the present invention has high flame retardancy that allows flame retardancy to be imparted to resins etc. with a small amount of addition and also has high hydrolysis resistance and favorable physical property values. Therefore, the fluorine-containing phosphate ester-amide is very useful for applications such as flame retardants for resins, flame retardants for flammable liquids, flame retardant solvents for organic synthesis, flame retardant solvents for electrolytes for secondary batteries, flame retardant hydraulic fluids, flame retardant lubricants, flame retardant extractants, and flame retardant cleaning agents.

The invention claimed is:

1. A fluorine-containing phosphate ester-amide selected from the group consisting of
   phosphoric acid bis(2,2,2-trifluoroethyl) diisopropylamide,
   phosphoric acid bis (2,2,2-trifluoroethyl) N-isopropyl-n-propylamide,
   phosphoric acid bis(2,2,2-trifluoroethyl) 2-methylpiperidide,
   phosphoric acid bis(2,2,2-trifluoroethyl) N-t-butylmethylamide,
   phosphoric acid bis(2,2,3,3-tetrafluoropropyl) diisopropylamide, and
   phosphoric acid bis(2,2,2-trifluoroethyl) N-isopropyl-2-methoxyethylamide.

2. A flame retardant resin composition, comprising a resin and a fluorine-containing phosphate ester-amide of claim 1.

3. A flame retardant liquid composition, comprising a liquid and a fluorine-containing phosphate ester-amide of claim 1.

4. A flame retardant solvent for organic synthesis, comprising a fluorine-containing phosphate ester-amide of claim 1 and a solvent for organic synthesis.

5. The flame retardant resin composition according to claim 2, comprising 2 to 20% by weight of said fluorine-containing phosphate ester-amide with respect to the weight of the resin.

6. The flame retardant resin composition according to claim 5, wherein the resin is selected from polyethylene resins, polyester resins, polyurethane resins, and phenolic resins.

7. The fluorine-containing phosphate ester-amide of claim 1, wherein said fluorine-containing phosphate ester-amide is phosphoric acid bis(2,2,2-trifluoroethyl) diisopropylamide.

8. The fluorine-containing phosphate ester-amide of claim 1, wherein said fluorine-containing phosphate ester-amide is phosphoric acid bis (2,2,2-trifluoroethyl) N-isopropyl-n-propylamide.

9. The fluorine-containing phosphate ester-amide of claim 1, wherein said fluorine-containing phosphate ester-amide is phosphoric acid bis(2,2,2-trifluoroethyl) 2-methylpiperidide.

10. The fluorine-containing phosphate ester-amide of claim 1, wherein said fluorine-containing phosphate ester-amide is phosphoric acid bis(2,2,2-trifluoroethyl) N-t-butyl-methylamide.

11. The fluorine-containing phosphate ester-amide of claim 1, wherein said fluorine-containing phosphate ester-amide is phosphoric acid bis(2,2,3,3-tetrafluoropropyl) diisopropylamide.

12. The fluorine-containing phosphate ester-amide of claim 1, wherein said fluorine-containing phosphate ester-amide is phosphoric acid bis(2,2,2-trifluoroethyl) N-isopropyl-2-methoxyethylamide.

* * * * *